United States Patent
Chon et al.

(10) Patent No.: US 9,283,113 B2
(45) Date of Patent: Mar. 15, 2016

(54) ULTRASONIC HAND PIECE

(71) Applicant: NOVARTIS AG, BASEL (CH)

(72) Inventors: James Chon, Irvine, CA (US); John Zhongyu Yan, Irvine, CA (US)

(73) Assignee: Novartis AG, Basel (CH)

( * ) Notice: Subject to any disclaimer, the term of this patent is extended or adjusted under 35 U.S.C. 154(b) by 154 days.

(21) Appl. No.: 14/284,541

(22) Filed: May 22, 2014

(65) Prior Publication Data

US 2015/0335483 A1  Nov. 26, 2015

(51) Int. Cl.
*A61B 17/32* (2006.01)
*A61F 9/007* (2006.01)
*A61B 17/00* (2006.01)

(52) U.S. Cl.
CPC ... *A61F 9/00745* (2013.01); *A61B 2017/00017* (2013.01); *A61B 2017/0046* (2013.01); *A61B 2017/00402* (2013.01); *A61B 2017/00477* (2013.01)

(58) Field of Classification Search
CPC ............ A61F 9/00745; A61F 9/00763; A61F 9/00736; A61F 9/00754; A61B 17/320068; A61B 2017/00017; A61B 2017/00402; A61B 2017/0046; A61B 2017/00477; A61B 2017/320096; A61B 2017/320072; A61B 17/320096; A61B 8/4483; B06B 3/00; B06B 3/02; B06B 3/04; B06B 1/0659; B06B 1/0622; B06B 1/0607; H01L 41/0833; H02N 2/106; H02N 2/108; A61N 2007/0043; A61C 1/07
USPC ............ 606/169; 604/22; 310/311, 367, 369, 310/370, 371, 323.12; 381/190
See application file for complete search history.

(56) References Cited

U.S. PATENT DOCUMENTS

| | | | | |
|---|---|---|---|---|
| 4,169,984 A * | 10/1979 | Parisi | ...................... | A61C 17/20 310/323.18 |
| 4,752,712 A * | 6/1988 | Tomita | ................. | H01L 41/0471 29/25.35 |
| 4,868,446 A * | 9/1989 | Kumada | ................. | H02N 2/002 310/323.02 |
| 4,961,424 A * | 10/1990 | Kubota | ............. | A61B 17/22012 601/2 |
| 5,371,429 A * | 12/1994 | Manna | ................... | B06B 1/0618 310/328 |
| 5,448,128 A * | 9/1995 | Endo | ..................... | H02N 2/0035 310/323.12 |
| 5,843,109 A * | 12/1998 | Mehta | .................... | B06B 1/0618 604/22 |
| 5,921,999 A * | 7/1999 | Dileo | ................... | A61F 9/00745 604/19 |
| 6,020,674 A * | 2/2000 | Zhang | ................. | H01L 41/0993 310/333 |
| 6,077,285 A * | 6/2000 | Boukhny | .............. | B06B 1/0611 604/22 |
| 6,190,497 B1 * | 2/2001 | Chan | ..................... | B06B 1/0622 156/580.1 |
| 6,402,769 B1 | 6/2002 | Boukhny | | |
| 7,627,936 B2 * | 12/2009 | Bromfield | ............. | B06B 1/0611 29/25.35 |
| 7,847,468 B2 * | 12/2010 | Kimura | ................. | B06B 1/0618 310/322 |
| 8,469,981 B2 * | 6/2013 | Robertson | ........ | A61B 17/22004 604/22 |
| 2001/0034532 A1 * | 10/2001 | Cimino | .......... | A61B 17/320068 606/169 |

(Continued)

*Primary Examiner* — Katrina Stransky
(74) *Attorney, Agent, or Firm* — Kenneth D. Bassinger

(57) ABSTRACT

A surgical hand piece comprises a generally cylindrical horn with a flange on one end. The flange has a central hub and first and second protruding sections. First and second polarized piezoelectric crystals are held against the flange such that rotative or torsional motion is induced in the horn.

14 Claims, 4 Drawing Sheets

(56) References Cited

U.S. PATENT DOCUMENTS

| | | | |
|---|---|---|---|
| 2002/0021328 A1* | 2/2002 | Aizawa | B41J 2/14008 347/46 |
| 2002/0149301 A1* | 10/2002 | Maruyama | H01L 41/0472 310/366 |
| 2007/0276252 A1* | 11/2007 | Kolasa | A61B 8/06 600/459 |
| 2008/0234711 A1* | 9/2008 | Houser | A61B 17/320068 606/169 |
| 2009/0149801 A1* | 6/2009 | Crandall | B06B 1/0611 604/22 |
| 2010/0004558 A1* | 1/2010 | Frankhouser | A61B 10/025 600/567 |
| 2010/0036256 A1* | 2/2010 | Boukhny | A61F 9/00745 600/459 |
| 2011/0239785 A1* | 10/2011 | Ting | G01L 3/10 73/862.325 |
| 2012/0065578 A1* | 3/2012 | Zhou | A61M 1/0064 604/22 |
| 2012/0209303 A1* | 8/2012 | Frankhouser | A61B 10/025 606/169 |
| 2013/0274637 A1* | 10/2013 | Akagane | A61B 17/320068 601/2 |
| 2014/0309562 A1* | 10/2014 | Ito | H01L 41/18 601/2 |
| 2015/0045701 A1* | 2/2015 | Akagane | A61B 17/320068 601/2 |
| 2015/0045806 A1* | 2/2015 | Urich | A61F 9/00745 606/107 |
| 2015/0088154 A1* | 3/2015 | Vaitekunas | A61B 17/12 606/128 |
| 2015/0196426 A1* | 7/2015 | Kuebler | A61F 9/00736 604/22 |

* cited by examiner

ULTRASONIC HAND PIECE

BACKGROUND OF THE INVENTION

This invention relates generally to the field of phacoemulsification and more particularly to ultrasonic hand pieces.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial lens (IOL).

In the United States, the majority of cataractous lenses are removed by a surgical technique called phacoemulsification. During this procedure, a thin phacoemulsification cutting needle is inserted into the diseased lens and vibrated ultrasonically. The vibrating cutting needle liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven hand piece, an attached cutting needle, an irrigating sleeve, and an electronic control console. The hand piece assembly is attached to the control console by an electric cable and flexible tubing. Through the electric cable, the console varies the power level transmitted by the hand piece to the attached cutting needle and the flexible tubing supply irrigation fluid to and draw aspiration fluid from the eye through the hand piece assembly.

The operative part of the hand piece is a centrally located, hollow resonating bar or horn directly attached to a set of piezoelectric crystals. The crystals supply the required ultrasonic vibration needed to drive both the horn and the attached cutting needle during phacoemulsification and are controlled by the console. The crystal/horn assembly is suspended within the hollow body or shell of the hand piece by flexible mountings. The hand piece body terminates in a reduced diameter portion or nosecone at the body's distal end. The nosecone is externally threaded to accept the irrigation sleeve. Likewise, the horn bore is internally threaded at its distal end to receive the external threads of the cutting needle. The irrigation sleeve also has an internally threaded bore that is screwed onto the external threads of the nosecone. The cutting needle is adjusted so that the needle projects only a predetermined amount past the open end of the irrigating sleeve.

In use, the ends of the cutting needle and irrigating sleeve are inserted into a small incision of predetermined width in the cornea or sclera. The cutting needle is ultrasonically vibrated along its longitudinal axis within the irrigating sleeve by the crystal-driven ultrasonic horn, thereby emulsifying the selected tissue in situ. The hollow bore of the cutting needle communicates with the bore in the horn that in turn communicates with the aspiration line from the hand piece to the console. A reduced pressure or vacuum source in the console draws or aspirates the emulsified tissue from the eye through the open end of the cutting needle, the cutting needle and horn bores and the aspiration line and into a collection device. The aspiration of emulsified tissue is aided by a saline solution or irrigating solution that is injected into the surgical site through the small annular gap between the inside surface of the irrigating sleeve and the cutting needle.

SUMMARY OF THE INVENTION

In one example of the present invention, a surgical hand piece comprises a generally cylindrical horn with a flange on one end, the flange having a central hub and first and second protruding sections, the first and second protruding sections each having first and second sides; a first piezoelectric crystal held against the horn, the first piezoelectric crystal having a semicircular shape with an inner circumference, an outer circumference, and first and second ends; a second piezoelectric crystal held against the horn, the second piezoelectric crystal having a semicircular shape with an inner circumference, an outer circumference, and first and second ends; wherein the inner circumference of the first piezoelectric crystal is held against a periphery of the hub, the first end of the first piezoelectric crystal is held against the first side of the first protruding section, and the second end of the first piezoelectric crystal is held against the first side of the second protruding section; and further wherein the inner circumference of the second piezoelectric crystal is held against a periphery of the hub, the first end of the second piezoelectric crystal is held against the second side of the first protruding section, and the second end of the second piezoelectric crystal is held against the second side of the second protruding section.

In other examples of the present invention, the first piezoelectric crystal is polarized along a circumferential direction from its first end to its second end, the second piezoelectric crystal is polarized along a circumferential direction from its first end to its second end, and/or the first and second piezoelectric crystals induce rotative or torsional motion in the horn.

In other examples of the present invention the surgical hand piece further comprises one or more of a needle coupled to the horn, a reduced diameter section of the horn, a needle interface coupled to the reduced diameter section of the horn, a nut that secures the first and second piezoelectric crystals to the horn, a first pair of lead wires coupled to the first piezoelectric crystal, and a second pair of lead wires coupled to the second piezoelectric crystal.

In other examples of the present invention, the first and second piezoelectric crystals induce a torsional or side-to-side motion at a distal tip of the needle; a first electric signal applied to the first pair of lead wires causes the first piezoelectric signal to vibrate along a first direction of polarization, and a second electric signal applied to the second pair of lead wires causes the second piezoelectric signal to vibrate along a second direction of polarization; the first direction of polarization is the same as the second direction of polarization; a polarity of the first electric signal is periodically reversed, and a polarity of the second electric signal is periodically reversed to induce rotative or torsional motion in the horn; and/or the first pair of lead wires is coupled to the first piezoelectric crystal at the first end of the first piezoelectric crystal; and the second pair of lead wires is coupled to the second piezoelectric crystal at the first end of the second piezoelectric crystal.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Reference is now made in detail to the exemplary embodiments of the invention, examples of which are illustrated in the accompanying drawings. Wherever possible, the same reference numbers are used throughout the drawings to refer to the same or like parts.

Figure 1:
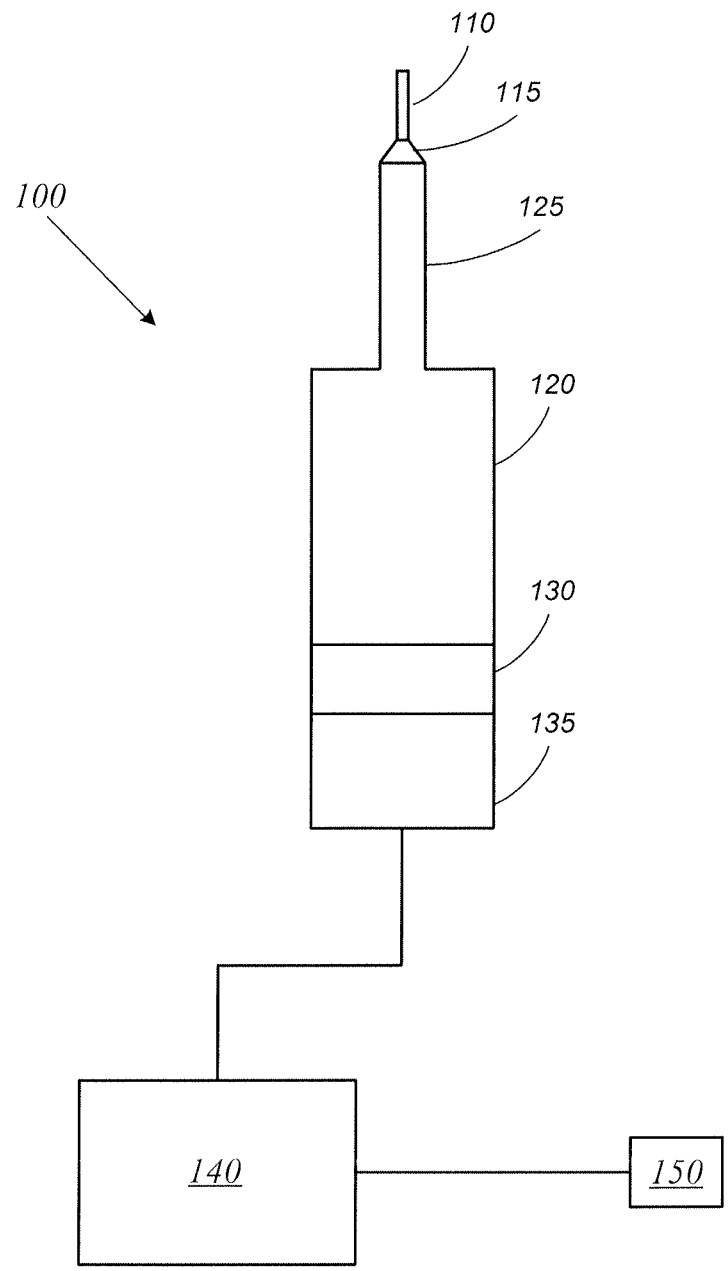
FIG. 1 is a diagram of a surgical hand piece system.

FIG. 1 depicts an ultrasonic hand piece system. In FIG. 1, hand piece 100 is coupled to console 140. Console 140 is coupled to foot switch 150. Hand piece 100 has a cutting needle 110, a horn 120, a set of piezoelectric crystals 130, and a nut 135 that secures the piezoelectric crystals 130 to the horn 120. A needle interface 115 connects cutting needle 110 to a reduced diameter portion 125 of horn 120.

Needle 110 is typically a thin needle made of titanium or stainless steel that is designed to emulsify a lens when vibrated ultrasonically. Needle 110 is typically cylindrical in shape, has a small diameter of about 20-30 gauge, and has a length suitable for removal of a lens when inserted into the anterior chamber of the eye.

Horn 120 is typically made of a rigid material suitable for medical use (such as a titanium alloy). Horn 120 has a reduced diameter section 125 that is connected to a needle interface 115. Needle interface 115 typically has a threaded connection that accepts needle 110. In this manner needle 110 is screwed onto horn 120 at needle interface 115. This provides a rigid connection between needle 110 and horn 120 so that vibration can be transmitted from horn 120 to needle 110.

Piezoelectric crystals 130 supply ultrasonic vibrations that drive both the horn 120 and the attached cutting needle 110 during phacoemulsification. Piezoelectric crystals 130 are secured against horn 120 by nut 135. Piezoelectric crystals 130 are typically constructed from a plurality of crystal segments. When excited by a signal from console 140, piezoelectric crystals 130 resonate, producing vibration in horn 120.

Console 140 includes a signal generator that produces a signal to drive piezoelectric crystals 130. Console 140 has a suitable microprocessor, micro-controller, computer, or digital logic controller to control the signal generator. In operation, console 140 produces a signal that drives piezoelectric crystals 130. Piezoelectric crystals 130, when excited, cause horn 120 to vibrate. Needle 110, connected to horn 120, also vibrates. When needle 110 is inserted into the anterior chamber of the eye and vibrated, it acts to emulsify a cataractous lens.

Figure 2:
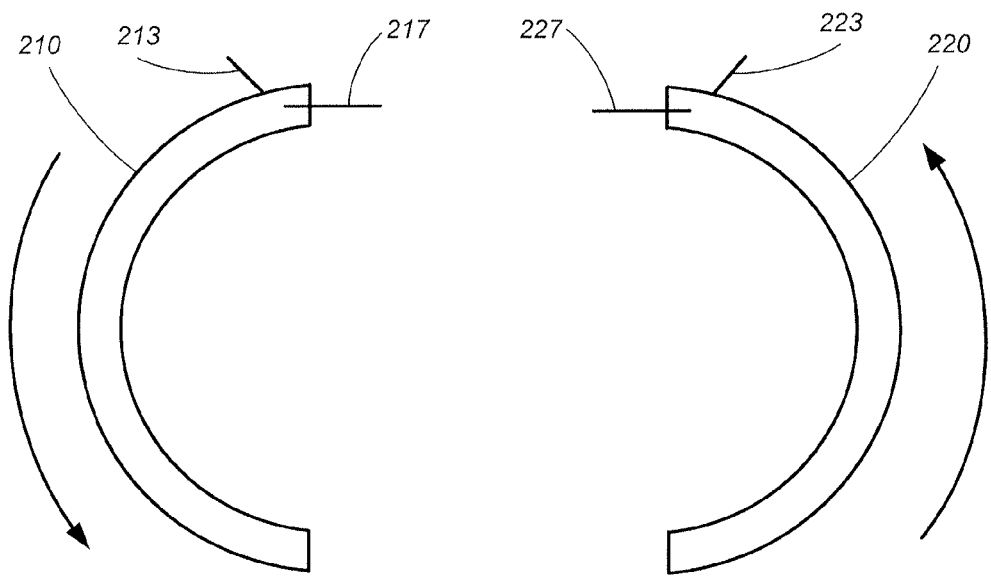
FIG. 2 is a side view of a pair of piezoelectric crystals.

FIG. 2 is a side view of a pair of piezoelectric crystals. Piezoelectric crystals 210, 220 are each generally semicircular in shape. Piezoelectric crystal 210 has a pair of lead wires 213, 217 electrically coupled to it. Lead wires 213 and 217 are located on opposite sides of the same end of piezoelectric crystal 210. Lead wires 213, 217 provide an electrical signal to piezoelectric crystal 210 that excites it and causes it to vibrate. In one example, the signal causes piezoelectric crystal 210 to vibrate ultrasonically. When piezoelectric crystal 210 is polarized, it vibrates in a specific manner (along an axis of polarization). In one example, piezoelectric crystal 210 is polarized along a circumference of the semicircle so that it produces vibration that is shown by the arrow. In this manner, piezoelectric crystal 210 vibrates in a direction along the arrow (or along the circumference of the semicircle).

Piezoelectric crystal 220 has a pair of lead wires 223, 227 electrically coupled to it. Lead wires 223 and 227 are located on opposite sides of the same end of piezoelectric crystal 220. Lead wires 223, 227 provide an electrical signal to piezoelectric crystal 220 that excites it and causes it to vibrate. In one example, the signal causes piezoelectric crystal 220 to vibrate ultrasonically. When piezoelectric crystal 220 is polarized, it vibrates in a specific manner (along an axis of polarization). In one example, piezoelectric crystal 220 is polarized along a circumference of the semicircle so that it produces vibration that is shown by the arrow. In this manner, piezoelectric crystal 220 vibrates in a direction along the arrow (or along the direction of the semicircle.

Piezoelectric crystals 210 and 220 cooperate to produce a torsional or rotative vibration. Piezoelectric crystal 210 is polarized along a first direction, and piezoelectric crystal 220 is polarized along a second, generally opposite direction. In this manner, the two piezoelectric crystals 210, 220 cooperate to produce a torsional or rotative vibration.

An electric signal or current is introduced to piezoelectric crystal 210 via lead wires 213, 217 to cause piezoelectric crystal 210 to vibrate along the direction in which it is polarized. Generally, this electric current flows through lead wire 213, through piezoelectric crystal 210, and out the other lead wire 217. When the polarity of the electric signal is reversed, the current flows through lead wire 217, through piezoelectric crystal 210, and out the other lead wire 213. In this case, piezoelectric crystal 210 vibrates in a direction opposite its polarity. An electric signal or current is introduced to piezoelectric crystal 220 via lead wires 223, 227 to cause piezoelectric crystal 220 to vibrate along the direction in which it is polarized. Generally, this electric current flows through lead wire 223, through piezoelectric crystal 220, and out the other lead wire 227. When the polarity of the electric signal is reversed, the current flows through lead wire 227, through piezoelectric crystal 220, and out the other lead wire 223. In this case, piezoelectric crystal 220 vibrates in a direction opposite its polarity.

By changing the polarity of the electric signals sent to piezoelectric crystals 210, 220, the crystals can be vibrated in one rotative direction (along the direction in which they are polarized) and then in the opposite direction (opposite the direction in which they are polarized). In this manner, a torsional or rotative motion can be induced in the cutting needle.

Figure 3:
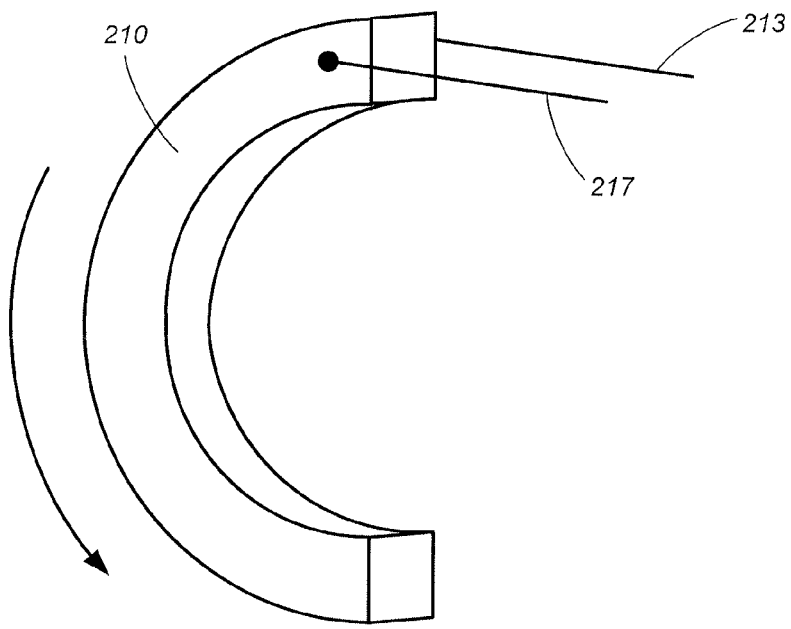
FIG. 3 is a perspective view of a piezoelectric crystal.

FIG. 3 is a perspective view of one piezoelectric crystal. In FIG. 3, piezoelectric crystal 210 is semicircular in shape and has a thickness. Piezoelectric crystal 210 is electrically coupled to a pair of lead wires 213, 217. Lead wires 213 and 217 are located on opposite sides of the same end of piezoelectric crystal 210. Lead wires 213, 217 provide an electrical signal to piezoelectric crystal 210 that excites it and causes it to vibrate. In one example, the signal causes piezoelectric crystal 210 to vibrate ultrasonically. When piezoelectric crystal 210 is polarized, it vibrates in a specific manner (along an axis of polarization). In one example, piezoelectric crystal 210 is polarized along a circumference of the semicircle so that it produces vibration that is shown by the arrow (i.e. it vibrates along the perimeter of the semicircle). In this manner, when a signal is applied via lead wires 213, 217, piezoelectric crystal 210 vibrates in a direction along the arrow.

Figure 4:
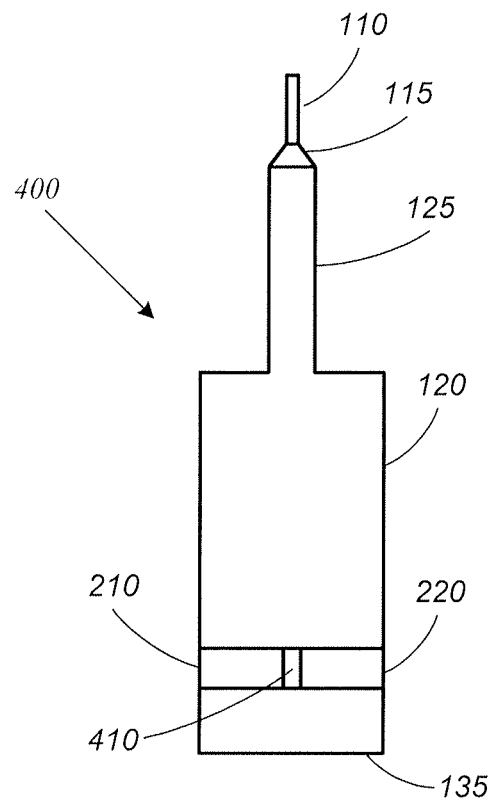
FIG. 4 is a side cross section view of a surgical hand piece.

FIG. 4 is a side cross section view of a surgical hand piece. In the example of FIG. 4, hand piece 400 has a cutting needle 110, a horn 120, a set of piezoelectric crystals 130, and a nut 135 that secures the piezoelectric crystals 210, 220 to the horn 120. A needle interface 115 connects cutting needle 110 to a reduced diameter portion 125 of horn 120. Flange 410 separates piezoelectric crystal 210 from piezoelectric crystal 220 and provides a surface against which piezoelectric crystals 210 and 220 can induce vibrations in horn 120.

Needle 110 is typically a thin needle made of titanium or stainless steel that is designed to emulsify a lens when vibrated ultrasonically. Needle 110 is typically cylindrical in shape, has a small diameter of about 20-30 gauge, and has a length suitable for removal of a lens when inserted into the anterior chamber of the eye.

Horn 120 is typically made of a rigid material suitable for medical use (such as a titanium alloy). Horn 120 has a reduced diameter section 125 that is connected to a needle interface 115. Needle interface 115 typically has a threaded connection that accepts needle 110. In this manner needle 110 is screwed onto horn 120 at needle interface 115. This provides a rigid connection between needle 110 and horn 120 so that vibration can be transmitted from horn 120 to needle 110.

Piezoelectric crystals 210 and 220 supply ultrasonic vibrations that drive both the horn 120 and the attached cutting needle 110 during phacoemulsification. Piezoelectric crystals 130 are secured against horn 120 by nut 135. Piezoelectric crystals 210 and 220 are polarized as previously described.

Figure 5:
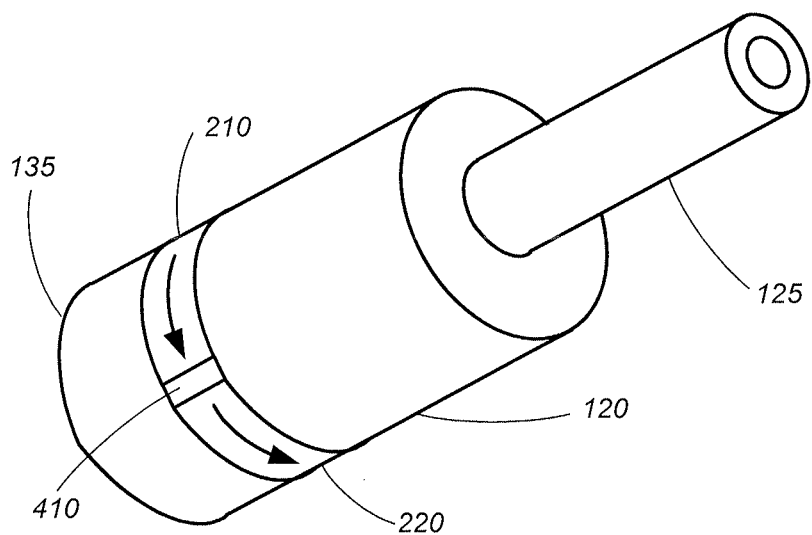
FIG. 5 is a perspective view of a portion of a surgical hand piece.

FIG. 5 is a perspective view of a portion of a surgical hand piece. In the example of FIG. 5, horn 120 has a reduced diameter section 125. A nut 135 secures piezoelectric crystals 210, 220 to horn 120. Flange 410 separates piezoelectric crystal 210 from piezoelectric crystal 220 and provides a surface against which piezoelectric crystals 210 and 220 can induce vibrations in horn 120.

Horn 120 is typically made of a rigid material suitable for medical use (such as a titanium alloy). Horn 120 has a reduced diameter section 125 that is connected to a needle interface as previously described.

Piezoelectric crystals 210 and 220 supply ultrasonic vibrations that drive both the horn 120 and the attached cutting needle 110 during phacoemulsification. Piezoelectric crystals 130 are secured against horn 120 by nut 135. Piezoelectric crystals 210 and 220 are polarized along a direction shown by the arrows as previously described.

Figure 6:
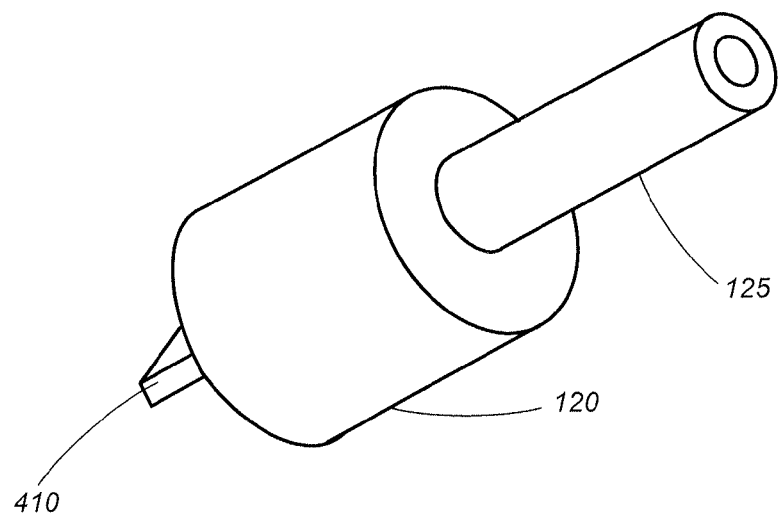
FIG. 6 is a perspective view of a horn of a surgical hand piece.

FIG. 6 is a perspective view of a horn of a surgical hand piece. In the example of FIG. 6, horn 120 has a reduced diameter section 125 and a flange 410. Flange 410 is configured to separate the two semicircular crystals 210, 220 (not shown) and provide a surface against which they can vibrate to induce a torsional or rotative vibration in horn 120. The configuration of flange 410 is more clearly shown in FIG. 7.

Figure 7:
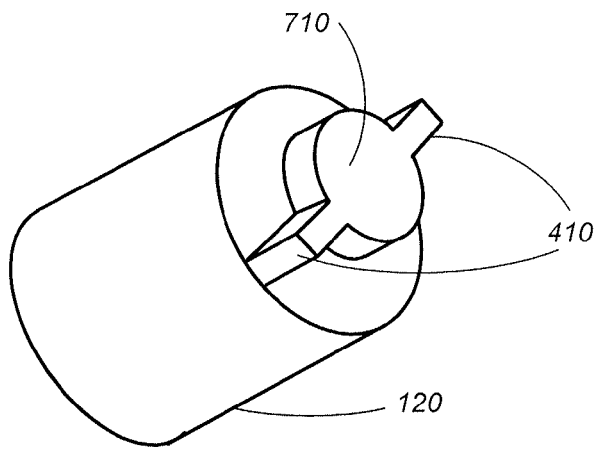
FIG. 7 is a perspective view of a partial horn of a surgical hand piece.

FIG. 7 is a perspective view of a partial horn of a surgical hand piece. In the example of FIG. 7, flange 410 is shown on an end of horn 120. Flange 410 has a central circular section or hub 710 and two protruding rectangular sections (designated as flange 410). The flange 410 provides a surface against which the peizeoelectric crystals 210, 220 (previously described) can vibrate. Since piezoelectric crystals 210, 220 are polarized along their respective circumferences, they vibrate against flange 410 in a manner than induces a torsional or rotative vibration in horn 120.

Figure 8:
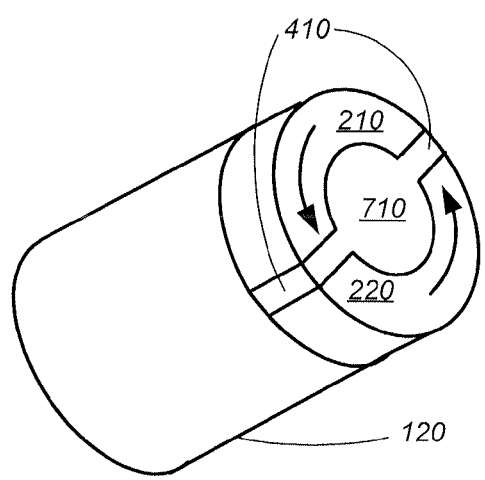
FIG. 8 is a perspective view of a partial horn with piezoelectric crystals.

FIG. 8 is a perspective view of a partial horn with piezoelectric crystals. In the example of FIG. 8, the location of piezoelectric crystals 210, 220 with respect to flange 410 is more clearly shown. Flange 410 has a central circular section or hub 710 and two protruding rectangular sections (designated as flange 410). The flange 410 provides a surface against which the peizeoelectric crystals 210, 220 (previously described) can vibrate. Since piezoelectric crystals 210, 220 are polarized along their respective circumferences in a direction as shown in the arrows, they vibrate against flange 410 in a manner than induces a torsional or rotative vibration in horn 210.

In FIG. 8, the inner circumference of piezoelectric crystal 210 contacts a periphery of hub 710. Likewise, the inner circumference of piezoelectric crystal 220 contacts a periphery of hub 710. In this manner, the piezoelectric crystals 210, 220 are held against hub 710. In addition, the two ends of piezoelectric crystal 210 contact one side of flange 410 (at the protruding rectangular section), and the two ends of piezoelectric crystal 220 contact the other side of flange 410 (at the protruding rectangular section). In this manner, piezoelectric crystals 210, 220 are held against flange 410 at the hub 710 and the protruding rectangular sections. In one example, a nut 135 holds piezoelectric crystals 210, 220 against flange 410 in this manner.

From the above, it may be appreciated that the present invention provides an improved surgical hand piece for cataract surgery. The present invention provides a hand piece with polarized semi-circular piezoelectric crystals that produce a torsional, rotational or back and forth cutting motion. The present invention is illustrated herein by example, and various modifications may be made by a person of ordinary skill in the art. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A surgical hand piece comprising:
   a generally cylindrical horn with a flange on one end, the flange having a central hub and first and second protruding sections, the first and second protruding sections each having first and second sides;
   a first piezoelectric crystal held against the horn, the first piezoelectric crystal having a semicircular shape with an inner circumference, an outer circumference, and first and second ends;
   a second piezoelectric crystal held against the horn, the second piezoelectric crystal having a semicircular shape with an inner circumference, an outer circumference, and first and second ends;
   wherein the inner circumference of the first piezoelectric crystal is held against a periphery of the hub, the first end of the first piezoelectric crystal is held against the first side of the first protruding section, and the second end of the first piezoelectric crystal is held against the first side of the second protruding section; and
   further wherein the inner circumference of the second piezoelectric crystal is held against a periphery of the hub, the first end of the second piezoelectric crystal is held against the second side of the first protruding section, and the second end of the second piezoelectric crystal is held against the second side of the second protruding section.

2. The surgical hand piece of claim 1 wherein the first piezoelectric crystal is polarized along a circumferential direction from its first end to its second end.

3. The surgical hand piece of claim 1 wherein the second piezoelectric crystal is polarized along a circumferential direction from its first end to its second end.

4. The surgical hand piece of claim 1 wherein the first and second piezoelectric crystals induce rotative or torsional motion in the horn.

5. The surgical hand piece of claim 1 further comprising:
a needle coupled to the horn.

6. The surgical hand piece of claim 5 wherein the first and second piezoelectric crystals induce a torsional or side-to-side motion at a distal tip of the needle.

7. The surgical hand piece of claim 1 wherein the horn further comprises a reduced diameter section.

8. The surgical hand piece of claim 7 further comprising:
a needle interface coupled to the reduced diameter section of the horn.

9. The surgical hand piece of claim 1 further comprising:
a nut that secures the first and second piezoelectric crystals to the horn.

10. The surgical hand piece of claim 1 further comprising:
a first pair of lead wires coupled to the first piezoelectric crystal; and
a second pair of lead wires coupled to the second piezoelectric crystal.

11. The surgical hand piece of claim 10 wherein a first electric signal applied to the first pair of lead wires causes the first piezoelectric signal to vibrate along a first direction of polarization, and a second electric signal applied to the second pair of lead wires causes the second piezoelectric signal to vibrate along a second direction of polarization.

12. The surgical hand piece of claim 11 wherein the first direction of polarization is the same as the second direction of polarization.

13. The surgical hand piece of claim 11 wherein a polarity of the first electric signal is periodically reversed, and a polarity of the second electric signal is periodically reversed to induce rotative or torsional motion in the horn.

14. The surgical hand piece of claim 10 wherein the first pair of lead wires is coupled to the first piezoelectric crystal at the first end of the first piezoelectric crystal; and the second pair of lead wires is coupled to the second piezoelectric crystal at the first end of the second piezoelectric crystal.

\* \* \* \* \*